US009962468B2

(12) United States Patent
Sabri

(10) Patent No.: US 9,962,468 B2
(45) Date of Patent: May 8, 2018

(54) CELL GROWTH APPARATUS AND USE OF AEROGELS FOR DIRECTED CELL GROWTH

(75) Inventor: Firouzeh Sabri, Lakeland, TN (US)

(73) Assignee: The University of Memphis Research Foundation, Memphis, TN (US)

(*) Notice: Subject to any disclaimer, the term of this patent is extended or adjusted under 35 U.S.C. 154(b) by 0 days. days.

(21) Appl. No.: 13/264,525

(22) PCT Filed: Apr. 15, 2010

(86) PCT No.: PCT/US2010/031253
§ 371 (c)(1),
(2), (4) Date: Jun. 4, 2012

(87) PCT Pub. No.: WO2010/121034
PCT Pub. Date: Oct. 21, 2010

(65) Prior Publication Data

US 2012/0231544 A1 Sep. 13, 2012

Related U.S. Application Data

(60) Provisional application No. 61/170,100, filed on Apr. 16, 2009.

(51) Int. Cl.

| | |
|---|---|
| ***A61L 27/56*** | (2006.01) |
| ***A61L 27/38*** | (2006.01) |
| ***C12M 1/12*** | (2006.01) |
| ***C12M 1/42*** | (2006.01) |
| ***C12N 5/00*** | (2006.01) |

(52) U.S. Cl.
CPC ............. *A61L 27/56* (2013.01); *A61L 27/383* (2013.01); *C12M 25/00* (2013.01); *C12M 35/08* (2013.01); *C12N 5/0068* (2013.01); *C12N 2535/10* (2013.01)

(58) Field of Classification Search
USPC .......................................................... 435/397
See application file for complete search history.

(56) References Cited

U.S. PATENT DOCUMENTS

| | | | | |
|---|---|---|---|---|
| 2003/0077312 A1* | 4/2003 | Schmulewicz et al. | ...... | 424/426 |
| 2007/0259328 A1* | 11/2007 | Morita et al. | .................. | 435/1.1 |
| 2008/0177371 A1 | 7/2008 | Ryan et al. | | |

FOREIGN PATENT DOCUMENTS

| | | | | | |
|---|---|---|---|---|---|
| EP | 0707474 B1 | * | 8/2000 | ............... | A61K 9/16 |
| EP | 1764116 | * | 3/2007 | ............. | A61L 27/28 |
| EP | 1764116 A1 | | 3/2007 | | |
| EP | 1800699 A1 | | 6/2007 | | |
| WO | WO9501165 | * | 1/1995 | ............... | A61K 9/16 |
| WO | 9712966 A1 | | 4/1997 | | |
| WO | WO9712966 | * | 4/1997 | ............. | C12N 11/14 |

OTHER PUBLICATIONS

Leventis et al. Durable modification of silica aerogel monoliths with fluorescent 2,7-diazapyrenium moieties. Sensing oxygen near the speed of open-air diffusion. Chem. Mater. 1999;11:2837-2845.*
Avnir et al. Recent bio-applications of sol-gel materials. J. Mater. Chem. 2006;16:1013-1030.*
Katti et al. Chemical, physical, and mechanical characterization of isocyanate cross-linked amine-modified silica aerogels. Chem. Mater. 2006;18:285-296.*
Li et al. Effects of three-dimensional scaffolds on cell organization and tissue development. Biotechnol. Bioprocess Eng. 2001;6:311-325.*
McKeehan et al. Stimulation of clonal growth of normal fibroblasts with substrata coated with basic polymers. The Journal of Cell Biology. 1976;71:727-734.*
Garreta et al. Synthesis of biocompatible surfaces by different techniques. Mat. Res. Soc. Symp. Proc. 2002;724:173-178.*
Rieckmann et al. Soluble forms of intercellular adhesion molecule-1 (ICAM-1) block lymphocyte attachment to cerebral endothelial cells. Journal of Neuroimmunology. 1995;60:9-15.*
Quinlan H. How aerogels work. HowStuffWorks. 2015;1-4.*
Cyostatin. Google search results. 2015;1-2.*
Yin et al. Biocompatibility of surfactant-templated polyurea-nanoencapsulated macroporous silica aerogels with plasma platelets and endothelial cells. J Biomed Mater Res A. 2010;92(4):1431-9.*
Levy D. New aerogel allows protein study outside normal environments. Stanford Report. 2004;1-3.*
Luo et al. The compressive behavior of isocyanate-crosslinked silica aerogel at high strain rates. Mech Time-Depend Mater. 2006;10:83-111.*
Bernik DL. Silicon based materials for drug delivery devices and implants. Recent Patents on Nanotechnology. 2007;1(3):186-192.*
Wang et al. Bio-MEMS fabricated artificial capillaries for tissue engineering. Microsyst Technol. 2005;12:120-127.*

* cited by examiner

*Primary Examiner* — Lynn Y Fan
(74) *Attorney, Agent, or Firm* — Mintz Levin Cohn Ferris Glovsky and Popeo, P.C.; Peter F. Corless

(57) ABSTRACT

This invention describes a cell growth apparatus, particularly neuronal printed circuit board apparatus comprising an aerogel base and a pre-printed cellular growth pattern. The cellular growth pattern is comprised of combinations of layers of cellular adhesion promoting materials, cellular adhesion inhibiting materials, and/or cellular signal promoting materials. The invention further describes methods of promoting cell growth using the neuronal printed circuit board apparatus of the invention. The invention is useful for regeneration and precise guidance of cells, particularly nerve cells, when used as an implant.

28 Claims, 12 Drawing Sheets

A

B

C a b c (a)

(b)

(c)

(d)

(e)

(f)

a)

b)

c)

d)

(a)

(b)

(c)

CELL GROWTH APPARATUS AND USE OF AEROGELS FOR DIRECTED CELL GROWTH

CROSS-REFERENCE TO RELATED APPLICATIONS

This application is a 35 U.S.C. § 371 U.S. national entry of International Application PCT/US2010/031253 (WO 2010/121034) having an International filing date of Apr. 15, 2010 which claims the benefit of U.S. Provisional Application No. 61/170,100, filed Apr. 16, 2009, the entire contents of which are incorporated herein by reference.

FIELD OF THE INVENTION

This invention relates to a cell growth apparatus, particularly neuronal printed circuit board apparatus comprising a porous substrate base and a pre-formed cellular growth and guidance pattern. The porous substrate base may be any porous substrate, including, but not limited to an aerogel. The cellular growth pattern is comprised of combinations of layers of cellular adhesion promoting materials, cellular adhesion inhibiting materials, and/or cellular signal promoting materials. The invention further describes methods of promoting cell growth using the neuronal printed circuit board apparatus of the invention. The invention provides materials useful for regeneration and precise guidance of cells, particularly nerve cells, when used in vivo (e.g., as an implant) or in vitro.

BACKGROUND OF THE INVENTION

Polymer crosslinked silica aerogels have been considered for various space-related applications due to their light weight (99.9% air) and yet high mechanical strength. Aerogels were invented in the 1930s and consist of a pearl-necklace-like network of skeletal nanoparticles, leaving more than 99% of their bulk volume empty. Chemically, the skeletal nanoparticles of most typical aerogels are made of silica. So far, the two major uses of aerogels have been as collectors of hypervelocity particles in space (Burchell 2009) upon NASA's Stardust Program and as thermal insulation of the electronic boxes on the Mars Rovers (Paul 2003). However, little work has been done on the biological applications of this class of materials.

Currently, materials of choice for nerve damage repair have been a variety of synthetic, polymeric, and biological [1-6] materials as well as those from the general category of hydrogels. Among the currently used implant materials, problems such as sagging, nerve pinching, and swelling of the implanted component itself have been reported. Similarly, large gaps can not be efficiently repaired, partially due to the fact that the implant material will potentially be too heavy. Furthermore, current materials are limited to a tubular (tunnel shaped) design which prevent the surgeon from seeing the nerve segments that are being handled once inserted into the implant. Finally, existing peripheral nerve repair devices require sutures for attaching the nerve stumps to the nerve repair device. Such suturing can lead to damage of the axons and require an intensely careful and well developed technique in order properly handle the nerve bundle.

As such, there is a need to develop novel implant materials and designs that avoid these problems and produce greater ease of use and provide a scaffold for cellular growth over larger distances.

BRIEF SUMMARY OF THE INVENTION

The present invention relates to the use of an aerogel as a base for the controlled growth of cells, particularly nerve cells.

The present invention further relates to the a substrate for cell growth, the substrate comprising a porous substrate base having one or a plurality of cellular adhesion promoting locations and at least one cellular adhesion inhibiting location.

In one aspect, the invention provides a substrate for cell growth, the substrate comprising an aerogel base having one or a plurality of cellular adhesion promoting locations and at least one cellular adhesion inhibiting location. In certain embodiments, the aerogel base is a hydrophobic aerogel base.

In still other embodiments, the substrate is an implant. In certain embodiments, the cellular adhesion promoting locations comprise a cellular adhesion promoting material disposed on the surface of the aerogel base. In certain embodiments, the cellular adhesion promoting locations comprise a cellular adhesion promoting material within the aerogel base. In certain embodiments, the cellular adhesion inhibiting location comprises a cellular adhesion inhibiting material disposed on the surface of, or within, the aerogel base. In certain embodiments, the substrate further comprises a cellular signal promoting material. In certain embodiments, the cellular adhesion promoting material, the cellular adhesion inhibiting material, and/or the cellular signal promoting material are disposed in one or more layers disposed on the aerogel base. In certain embodiments, the one or more layers are printed layers.

In one aspect, the invention provides a neuronal circuit board apparatus comprising an porous substrate base, a pre-printed directional growth pattern and a plurality of cellular adhesion locations situated at the ends of the pre-printed directional growth pattern.

In one aspect, the invention provides a neuronal circuit board apparatus comprising an aerogel base, a pre-printed directional growth pattern and a plurality of cellular adhesion locations situated at the ends of the pre-printed directional growth pattern.

In some embodiments, the aerogel base of the apparatus of the invention is a hydrophobic aerogel base. In some embodiments, the aerogel base is a silica aerogel base. In certain embodiments, the silica aerogel base is crosslinked with a polyurea.

In certain embodiments, the neuronal circuit board apparatus is in the form of an implant, including, but not limited to, a cell-scaffold, a joint-scaffold, an organ-scaffold, or a stent.

In yet another embodiment, the pre-printed directional growth pattern of the apparatus of the invention comprises at least one layer of an adhesion promoting material; at least one layer of an adhesion inhibiting material; and/or at least one layer of a cellular signal promoting material. The layers can be deposited in the same or different areas of the substrate.

In certain embodiments, the neuronal circuit board apparatus comprises at least two cellular adhesion locations; at least 4 cellular adhesion locations; or from 2 to 100 cellular adhesion locations.

In certain embodiments, the cellular adhesion locations are grouped such that two or more cellular adhesion locations are complimentary for the same cell type. In some embodiments, the neuronal circuit board apparatus of the invention comprises at least two sets of complementary cellular adhesion locations which are complimentary for different cell types.

In certain embodiments, the neuronal circuit board apparatus of the invention is pigmented or tinted such that the apparatus can be color coded. In certain embodiments, the complementary cellular adhesion locations are color coded to identify the start and end of a directional growth pattern. In certain embodiments, the pre-printed directional growth pattern is color coded to identify the directional growth pattern associated with complementary cellular adhesion locations. In some embodiments, the neuronal circuit board apparatus of the invention is pigmented, tinted or doped with metal oxide pigments, mixed metal oxide pigments, azurite pigments, red earth pigments, yellow earth pigments, metal complex dyes, carbon black, synthetic iron oxide pigments, ultramarine pigments or other inorganic pigments. In other embodiments, the neuronal circuit board apparatus of the invention is pigmented, tinted or doped non-metal based pigments or organic pigments, including but not limited to vegetable dyes, acid dyes, basic dyes, azoic Dyes, and sulphur Dyes.

BRIEF DESCRIPTION OF THE DRAWINGS

In FIG. 9(*a*)-9(*b*), a substrate is positioned to connect (a) dendrites of one neuron terminal buttons of another or (b) in between separated axon segments; (d) a tube-shaped substrate of the invention in which the opening behaves as a scaffold for the neuron; (e) a tube-shaped substrate of the invention having a bend in which the opening behaves as a scaffold for the neuron; (f) a neuronal circuit board of the invention in which dendrites of one neuron and dendrites of another are adhered to a directional growth pattern. After a period of time, the repaired axon (c) will form a continuous chain guided and supported by the aerogel substrate. Similarly, the repaired axon in (f) will follow the growth pattern to the merge point and continue on through the branch.

DETAILED DESCRIPTION OF THE INVENTION

Figure 1:
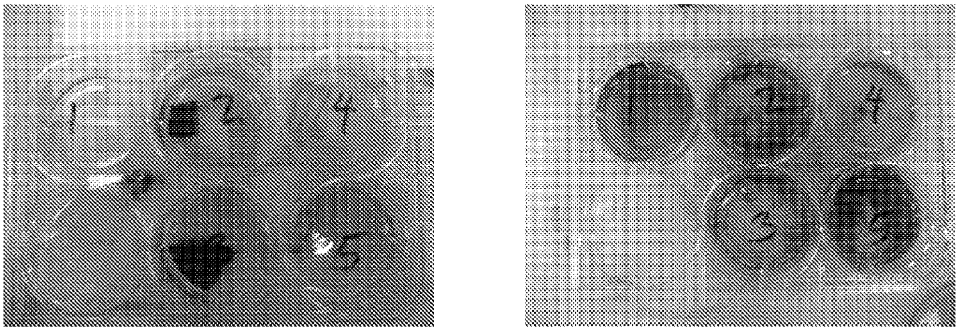
FIG. 1 is a depiction of sample wells showing of the effect of floating aerogels on opossum kidney (OK) cell growth: OK cells were plated in 6 well dishes in the absence or presence of pigmented aerogels. Forty-eight hrs after plating, the aerogels were removed and the OK cell monolayers were stained with 0.04% crystal violet.

The neuronal "printed circuit board" apparatus of the present invention provides advantages over traditional implants in that an porous substrate based apparatus described herein is lightweight and allows for the flow of vital fluids through the porous material, which can minimize swelling and nerve pinching associated with traditional implants. Furthermore, it is possible to reliably color-code these substrates through adding pigments (such as oxide-based pigments), e.g., at the synthesis stage, so the materials may be tinted to allow for color-coding of implants for various cell types to allow for easy recognition by a surgeon.

Furthermore, the light weight nature of aerogels, as well as their mechanical strength, adjustable pore size, hydrophobicity and the ability to create different geometries makes them excellent choices for many implant applications including the neuronal "printed circuit board" apparatus of the present. These properties can in turn prevent sagging at the implant site, allow exchange of vital fluids between the implant and its surrounding, as permit clear identification of the implanted unit based on its color. The mesh form structure of aerogels will also allow better anchorage for the regenerating cells or tissues, including, e.g., nerve fibers.

Definitions

As used herein the term "substrate" describes a material on which cells are to be attached and grown, e.g., as described herein. A substrate may be capable of use in the body of a subject (i.e. as an implant) or may be for use in a laboratory or other appropriate location (e.g., as in a petri dish). In certain embodiments, the "substrate" may be a neuronal or cellular circuit board as described herein.

As used herein, the term "neuronal circuit board" or "cellular circuit board" describes an implant device to which various cell types can be adhered, including but not limited to nerve cells, and which acts to promote cellular growth along a pre-determined path.

As used herein, the terms "porous material" and "porous base" describe a class of materials having a naturally or manually engineered porous structure that allows the flow of fluids and/or gasses across the material. The pores of the porous material may be continuous or not. Any material with naturally forming or artificially created pores. Porous materials can be provided at least in powder, granular, bead, and other suitable forms and include inorganic, organic, and hybrid organic-inorganic compositions, or some combination of the above forms and/or compositions.

As used herein, the terms "aerogel" and "aerogel base" describe a class of materials having a low density, open cell structures, large surface areas, and nanometer scale pore sizes. Aerogel materials can be provided at least in powder, granular, bead, and other suitable forms, and include inorganic, organic, and hybrid organic-inorganic compositions, or some combination of the above forms and/or compositions.

As used herein, the term "cellular adhesion location" refers to a portion of the aerogel base to which cells can be adhered. The cellular adhesion location can be an untreated portion of the porous base or aerogel base (e.g., if the porous base or aerogel materials is such that cells can attach to the untreated material) or it can be a region which has been treated (e.g., with an adhesion promoting material) so as to allow cells to be adhered to the porous base or aerogel base. In general, any given porous base or aerogel base will have at least two cellular adhesion locations. In other embodiments, a given porous base or aerogel base may comprise two different types of cellular adhesion locations to allow for different types of cells to be grown on the same porous base or aerogel base.

As used herein, the term "pre-printed directional growth pattern" and "pre-determined growth path" refers to the combination of adhesion promoting materials, adhesion inhibiting materials and signal promoting materials, including metal interconnects, and the pattern on which they are located a given porous base or aerogel base which corresponds to the pattern to which adhered cells will grow along the porous base or aerogel base. In some embodiments, the pre-printed directional growth pattern allows cells adhered to two or more cellular adhesion locations to grow to the same point on the porous base or the aerogel base. In certain embodiments, the pre-printed directional growth pattern allows cells adhered to different cellular adhesion locations to grow in such a way as to avoid overlap.

As used herein, the term "adhesion promoting material" is any material which may be applied to, incorporated into, or coated onto the porous base or the aerogel base which can create, assist, or promote adhesion of cells to the porous base or the aerogel base. The adhesion promoting material is selected depending on the types of cells to be adhered and the nature and shape of the porous base or the aerogel base. Furthermore, the adhesion promoting material may be selected based on the intended location of the cell growth, for example in vivo use of an implant or in vitro growth in a cell culture plate or other non-implanted means. Also, the adhesion promoting material may be a biological adhesive material or a non-biological adhesive. Exemplary adhesion promoting materials include, but are not limited to, poly-L-lysine, polyphenolic proteins secreted by *Mytilus edulis*, MAC-2 binding protein, laminin 10/11, albumin/glutaraldehyde tissue adhesive, fibrin tissue adhesive, cyanoacrylate-based tissue adhesive, proteinaceous adhesives such as the material sold under the trade name "Cell-Tak", and basement membrane extract (BME). Other adhesion promoting materials include, but are not limited to, immunoglobulin superfamily cellular adhesion molecules, integrins, cadherins, and selectins. Other adhesion materials include dental adhesives such as cyanoacrylate adhesives. Combinations of one or more adhesion promoting materials can also be employed, e.g., a combination of poly-L-lysine and BME.

As used herein, the term "adhesion inhibiting material" is any material which may be applied to, incorporated into, or coated onto the porous base or the aerogel base which can prevent or diminish adhesion of cells to the porous base or the aerogel base. The adhesion inhibiting material is selected depending on the types of cells to be adhered and the nature and shape of the porous base or the aerogel base. Furthermore, the adhesion inhibiting material may be selected based on the intended location of the cell growth, for example in vivo use of an implant or in vitro growth in a cell culture plate or other non-implanted means. Exemplary adhesion inhibiting materials include chondroitin sulfate dipalmitoylphosphatidylethanolamine, 1-alcohols, polynorbornenes, recombinant soluble intercellular adhesion molecule-1 (sICAM-1), cyostatin, or plasmogen activator inhibitor type-1 (PAI-1). Combinations of one or more adhesion promoting materials can also be employed. In certain embodiments, the adhesion inhibiting material may be the aerogel or porous material itself.

As used herein, the term "cellular signal promoting material" is any material which may be applied or coated onto the porous base or the aerogel base which can promote cell growth of cells to the aerogel base. The signal promoting material is selected depending on the types of cells to be grown, the desired speed and amount of growth, and the nature and shape of the aerogel base. Furthermore, the signal promoting material may be selected based on the intended location of the cell growth, for example in vivo use of an implant or in vitro growth in a cell culture plate or other non-implanted means. In certain embodiments, the signal promoting material and the adhesion promoting material may be the same material. In other embodiments, the signal promoting material and the adhesion promoting materials may be blended together and applied to the aerogel base at the same time, for example in the same layer or coating. Exemplary cellular signal promoting materials include, but are not limited to, insulin, transferrin, bone morphogenetic proteins (BMPs), epidermal growth factor (EGF), erythropoietin (EPO), fibroblast growth factor (FGF), granulocyte-colony stimulating factor (G-CSF), granulocyte-macrophage colony stimulating factor (GM-CSF), growth differentiation factor-9 (GDF9), hepatocyte growth factor (HGF), insulin-like growth factor (IGF-1, IGF-2), myostatin (GDF-8), nerve growth factor (NGF) and other neurotrophins, platelet-derived growth factor (PDGF), thrombopoietin (TPO), transforming growth factor alpha (TGF-α), transforming growth factor beta (TGF-β), vascular endothelial growth factor (VEGF), interleukins (IL-1α, IL-1β, IL-2, IL-3, IL-4, IL-5, IL-6, IL-7, IL-8, IL-9, IL-10, IL-11, IL-12, IL-13, IL-14, Il-15, IL-16, IL-17, IL-18), interferons, adipocytokines (leptin, adiponectin, resistin, visfatin, adipsin, MCP-1, PAL-1, CRP, receptor tyrosine kinases, receptor serine/threonine kinases, or PI3K.

Porous Materials

The porous base of the present invention can be any biocompatible organic, inorganic, metallic, polymeric or composite porous material. In certain embodiments, the porous materials have a naturally or manually engineered porous structure or scaffold that allows the flow of fluids and/or gasses across the material. The pores of the porous material may be continuous or not. The porosity should be sufficient to facilitate tissue ingrowth when deployed within an intracorporeal cavity. Porosity can have a pore size ranging from about 10 nanometers to about 600 micrometers. The surface pores are typically about 20 nanometers to about 80 micrometers and the interior pores are about 20 nanometers to about 200 micrometers. In certain embodiments, Porosity can have a pore size ranging from about 10 nanometers to about 10000 nanometers. Implant porosity is generally formed in the implant prior to deployment within the body cavity in order to control the size and shape of the implant.

In certain embodiments, the porous base materials can be a plastic material including, but not limited to: PET, polethylene terephthalate; PBT, polybutylene terephthalate; PSU, polysulfone; PES, polyethersulfone; PAS, polyarylsulfone; PPS, polyphenylene sulfide; PC, polycarbonate; PA, polyamide; PAI, polyamide-imide; TPI, thermoplastic polyimide; PAEK, polyaryletherketone; PEEK, polyetheretherketone; PAEN, polyarylethernitrile; PE, polyethylene; PP, polypropylene; and PEK, polyetherketone.

In other embodiments, the porous material may be selected from organic materials. Such materials can include, for example, biocompatible polymers, oligomers, or pre-polymerized forms as well as polymer composites. The polymers used may be thermosets, thermoplastics, synthetic rubbers, extrudable polymers, injection molding polymers, moldable polymers, spinnable, weavable and knittable polymers, oligomers or pre-polymerizes forms and the like or mixtures thereof.

In other embodiments, the porous materials may be biodegradable organic materials, including, but not limited to, chitosan, alginate, collagen, albumin, gelatine, hyaluronic acid, starch, cellulose (methylcellulose, hydroxypropylcellulose, hydroxypropylmethylcellulose, carboxymethylcellulose-phtalate); furthermore casein, dextrane, polysaccharide, fibrinogen, poly(D,L lactide), poly(D,L-lactide-Co-glycolide), poly(glycolide), poly/hydroxybutylate), poly(alkylcarbonate), poly(orthoester), polyester, poly(hydroxyvaleric acid), polydioxanone, poly(ethylene, terephtalate), poly(maleic acid), poly(tartaric acid), polyanhydride, polyphosphohazene, poly(amino acids), poly(L-lactic acid), polycaprolactone, poly(lactide-co-glycolide), poly(hydroxybutyrate), poly (hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly (iminocarbonate), copoly(ether-esters), polyalkylene oxalates, and polyphosphazenes, and all of the copolymers and any mixtures thereof. In certain embodiments, the porous base material is chitosan or collagen.

In certain other embodiments, the porous base material can be a porous ceramic, glass, or metal material, including, but not limited to, metals and metal alloys selected from main group metals of the periodic system, transition metals, such as copper, gold and silver, titanium, zirconium, hafnium, vanadium, niobium, tantalum, chromium, molybdenum, tungsten, manganese, rhenium, iron, cobalt, nickel, ruthenium, rhodium, palladium, osmium, iridium or platinum, or from rare earth metals. The material may also be selected from any suitable metal or metal oxide or from shape memory alloys any mixture thereof to provide the structural body of the implant. In certain embodiments the material is selected from the group of zero-valent metals, metal oxides, metal carbides, metal nitrides, metal oxynitrides, metal carbonitrides, metal oxycarbides, metal oxynitrides, metal oxycarbonitrides and the like, and any mixtures thereof. The metals or metal oxides or alloys used may be magnetic. Examples can include—without excluding others—iron, cobalt, nickel, manganese and mixtures thereof, for example iron, platinum mixtures or alloys, or for example, magnetic metal oxides like iron oxide and ferrite. In certain embodiments, the materials may be semi-conducting materials or alloys, for example semi-conductors from Groups II to VI, Groups III to V, and Group IV. Suitable Group II to VI semi-conductors are, for example, MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, HgTe, or mixtures thereof. Examples for suitable Group III to V semi-conductors are GaAs, GaN, GaP, GaSb, InGaAs, InP, InN, InSb, InAs, RIAs, AlP, AlSb, AlS and mixtures thereof. Examples for Group IV semi-conductors are germanium, lead and silicon. The semi-conductors may also comprise mixtures of semi-conductors from more than one group and all the groups mentioned above are included.

In still other embodiments, the porous material can include at least one of stainless steel, tantalum, titanium, nitinol, gold, platinum, inconel, iridium, silver, tungsten, or another biocompatible metal, or alloys of any of these; carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these.

Aerogels

The aerogel base of the present invention can be any biocompatible polymeric material comprising an open interconnected macroporous system with mesoporous walls. In general, aerogel bases of the present invention are silica aerogels which are generally low-density mesoporous solids formed as wet silica gels and dried through supercritical fluid extraction of the pore-filling gelation solvent. The aerogels can also be formed by replacing the supercritical drying stage with oven drying, or, controlled atmospheric drying.

In certain embodiments, the aerogels of the present invention are hydrophobic aerogels including, but not limited to polymer crosslinked aerogels $\alpha$-aerogels). In still other embodiments, the hydrophobic aerogel is a poly-urea x-aerogel.

The aerogel base of the present invention may be produced by any method, some of which are known in the art. In particular, x-aerogels may be produced by known procedures, such as those found in Leventis, N. et al. Nano Lett. 2002, 2, 957-960; Meador, M. A. B. et al. Chem. Mater. 2007, 19, 2247-2260; and Leventis, N. Acc. Chem. Res. 2007, http://dx.doi.org/10.1021/ar600033s.

Physical Parameters

The porous base or the aerogel base of the present invention may be formed into any size and shape desirable. In particular, the porous base or the aerogel base can be in the form of a square, rectangle, oblong, diamond, triangle, circle, or oval plate or sheet having a thickness ranging from 1 μM to about 5 μM. In certain embodiments the thickness of the porous base or the aerogel base is from 1 μM to 100 μM. In other embodiments, the thickness of the porous base or the aerogel base is from 1 mM to about 5 mM. In certain embodiments, the porous base or the aerogel base can be formed into a tube or series of interconnecting tubes. In still other embodiments, the porous base or the aerogel base can be formed by two plates of the same or different size and shape so that cells are grown through the space between the two plates. In embodiments wherein the porous base or the aerogel base is in the form of a tube, the thickness of the walls of the aerogel base tube is generally from 1 μM to about 3 mM with an overall diameter of about 1 μM to 5 μM.

In certain embodiments, the porous or the aerogel base is biocompatible, e.g., a material that has low or no toxicity to host tissue. In certain embodiments, the porous base or the aerogel is non-toxic, non-irritating, and non-allergenic. In certain embodiments, the porous base or the aerogel can be biodegradable, e.g., capable of dissolving or degrading in the body, preferably degrading to non-toxic products. The biocompatible and/or biodegradable properties of a porous base or an aerogel can be modified by changing the materials used to make the material, e.g. for aerogels, by changing the cross-linking reagent to provide an aerogel with altered properties.

Dyes and Tinting

In certain embodiments, the porous base or the aerogel base may be tinted using the methods described herein. Such tinting may be of any color desired for the particular application.

In certain embodiments, the neuronal circuit board apparatus of the invention is pigmented or tinted such that the apparatus can be color coded. In certain embodiments, the complementary cellular adhesion locations are color coded to identify the start and end of a directional growth pattern. In certain embodiments, the pre-printed directional growth pattern is color coded to identify the directional growth pattern associated with complementary cellular adhesion locations. In some embodiments, the neuronal circuit board apparatus of the invention is pigmented, tinted or doped with metal oxide pigments, mixed metal oxide pigments, azurite pigments, red earth pigments, yellow earth pigments, metal complex dyes, carbon black, synthetic iron oxide pigments, ultramarine pigments or other inorganic pigments. In other embodiments, the neuronal circuit board apparatus of the invention is pigmented, tinted or doped non-metal based pigments or organic pigments, including but not limited to vegetable dyes, acid dyes, basic dyes, azoic Dyes, and sulphur Dyes.

Exemplary pigments include, but are not limited to, Chromium oxide (green), iron-oxide (red), and cobalt oxide (blue) In some embodiments, a particular the porous or the aerogel base may be tinted using more than one color when more than one type of cell is to be adhered. Similarly, the porous or the aerogel may be tinted entirely or may be tinted only along the directional growth path for the particular cell growth.

Substrates or Neuronal or Cellular Circuit Boards

The substrate or the neuronal or cellular circuit board of the present invention may be provided with a pre-printed directional growth pattern in a manner appropriate for the particular cells to be adhered to or grown on the porous base or the aerogel base.

In certain embodiments, the substrate or the neuronal circuit board of the invention can be produced by providing a porous base or an aerogel base and a. applying an adhesion promoting material to the base in a pre-deter wined pattern;
b. optionally applying an adhesion inhibiting material to the base in a second pre-determined pattern; and
c. optionally applying a cellular signal promoting material to the base in a pattern which substantially overlaps the pattern of the adhesion promoting material.

In certain embodiments, the substrate or the neuronal circuit board of the invention can be produced by providing a porous base or an aerogel base and a. applying an adhesion promoting material to the base at specific cellular adhesion locations;
b. applying an cellular signal promoting material to the base in a pre-determined pattern; and
c. optionally applying an adhesion inhibiting material to the base in a second pre-determined pattern.

Figure 8:
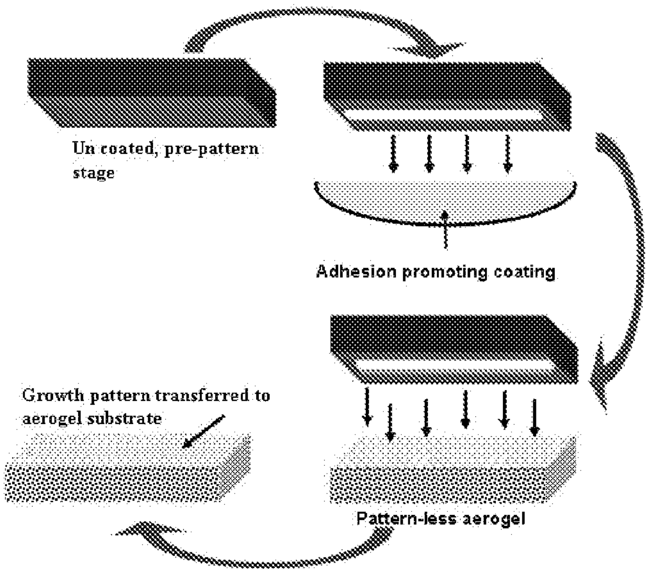
FIG. 8 is a depiction of the production of a substrate or neuronal or cellular circuit board of the present invention using a lithographic process for application of the adhesion promoting, adhesion inhibiting and/or signal promoting materials.

In certain embodiments, the adhesion promoting material, the adhesion inhibiting material and/or the signal promoting materials are applied to the aerogel base such that the functionality of the material is available for adherence of one or more cells. Such methods of application include, but are not limited to, coating, layering, depositing, embedding, implanting, impregnating, doping, or infusing the materials into the aerogel base or onto the surface of the aerogel base. In particular embodiments, the adhesion promoting material, the adhesion inhibiting material and/or the signal promoting materials are applied to the aerogel base via lithographic methods similar to those well known in the art. An exemplary scheme depicting a lithographic-type process is shown in FIG. 8. It will be appreciated that the adhesion promoting material, the adhesion inhibiting material and/or the signal promoting materials, when used, can be applied to any surface of the substrate or implant, as needed; in the case of a hollow (e.g., tubular or cup-shaped) substrate, the adhesion promoting material, the adhesion inhibiting material and/or the signal promoting materials can be applied to an interior or exterior surface as required.

In certain embodiments, the porous base or the aerogel base is molded such that the growth pattern becomes part of the shape of the base in the form of a channel or a series of channels and the adhesion inhibiting material and/or the signal promoting materials are cast into the channels. In other embodiments, the growth pattern is removed from the base by etching, carving, coring, boring, embossing, or other physical or chemical means of surface modification such that the adhesion inhibiting material and/or the signal promoting materials may then be cast into the resulting channels, holes, divots or gaps.

The adhesion inhibiting material, the adhesion promoting material, and/or a signal promoting material may be applied onto the surface of an base by any means known in the polymer arts. For example, the material(s) may be spray coated, screen coated, or stamped onto the aerogel base. Similarly, the material(s) may be annealed or cured onto the surface of the base. Further, the material(s) may be implanted, injected, absorbed or adsorbed into or onto the base such that the functionality of the material is maintained on the surface of the base.

In certain embodiments, the neuronal circuit board of the invention can be produced by coating the entire area of one surface of the porous base or the aerogel base with an adhesion promoting material, a signal promoting material, or a mixture of both and selectively applying an adhesion inhibiting material to the coated surface to produce the pattern.

In other embodiments, the neuronal circuit board of the invention can be produced by coating the entire area of one surface of the porous base or the aerogel base with an adhesion inhibiting material and selectively applying an adhesion promoting material, a signal promoting material, or a mixture of both materials to the coated surface to produce the pattern.

In embodiments where the porous base or the aerogel base is in the form of a tube or a series of interconnecting tubes, the external surface of the tubes may be coated with the adhesion inhibiting material while the internal surface of the tubes may be coated with the adhesion promoting material and/or the signal promoting material.

In embodiments where the porous base or the aerogel base is in the form of two plates to which the cells are adhered and grown between the plates, one plate may be coated with the directionalized pattern of adhesion promoting materials and adhesion inhibiting materials while the second plate may be coated with a directionalized pattern of signal promoting materials. Similarly, the second plate may be coated entirely with the signal promoting material.

The pattern provided on the porous base or the aerogel substrate is selected to promote or regulate cell growth in a desired pattern or direction. For example, the pattern can be selected to provide for directional growth of cells, e.g., to cause cells to grow toward each other or toward a particular location. For example, an implant for promoting regrowth of a severed nerve could include a pattern on the substrate selected to promote the growth of the severed ends of the nerve toward each other, to promote regeneration of the nerve. It is also possible to promote the growth of cells in two or three dimensions by using an appropriate pattern (and an appropriately shaped substrate).

In certain embodiments, growth factors, such as laminin, can be inserted into the pattern by micropipette, needle, syringe or other methods such as spin coating.

Figure 9:
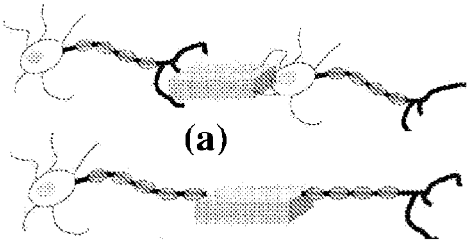
FIG. 9 depicts aerogel substrates of the invention.
Figure 9:
Figure 9:
Figure 9:
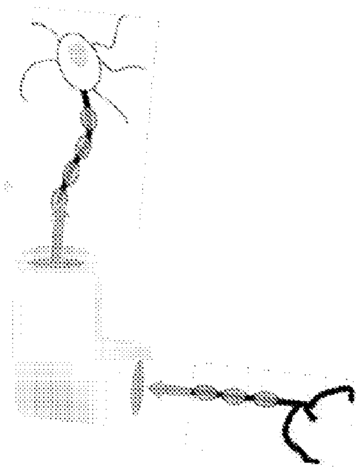
Figure 9:
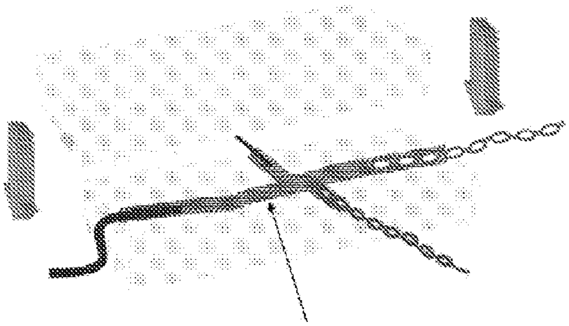

Examples of growth of cells or tissue are illustrated in FIG. 9. As shown in FIG. 9(*d*), an aerogel substrate can be used to guide an axon through a tube-shaped opening, thus acting as a scaffold for the neuron. FIG. 9 depicts aerogel substrates of the invention. In FIG. 9(*a*)-9(*b*), a substrate is positioned to connect (a) dendrites of one neuron terminal buttons of another or (b) in between separated axon segments; (d) a tube-shaped substrate of the invention in which the opening behaves as a scaffold for the neuron; (e) a tube-shaped substrate of the invention having a bend in which the opening behaves as a scaffold for the neuron; (f) a neuronal circuit board of the invention in which dendrites of one neuron and dendrites of another are adhered to a directional growth pattern. After a period of time, the repaired axon (c) will form a continuous chain guided and supported by the aerogel substrate. Similarly, the repaired axon in (f) will follow the growth pattern to the merge point and continue on through the branch.

Methods of Use

In certain embodiments, the substrate or the neuronal or cellular pre-printed circuit boards can be used to promote cell growth or tissue regeneration either in vivo or in vitro.

When used as an implant or a joint scaffold, the substrate or the neuronal circuit board can be implanted into a subject such that the cellular adhesion locations come into contact with the particular cell type to be grown. Such cells include, but are not limited to, neuron cells, skin cells, muscle cells, mucosal tissue cells, myofibers, hepatocytes, Sensory transducer cells, osteocytes, Autonomic neuron cells, Sense organ cells, peripheral neuron supporting cells, astrocytes, oligodendrocytes, Spindle neurons, Anterior lens epithelial cells, Crystallin-containing lens fiber cells, or interstitial cells.

In certain embodiments, the cells or tissues may be adhered to the substrate or the neuronal circuit board with the assistance of sutures or stitches. In other embodiments, the cells may be adhered to the substrate or the neuronal circuit board using a sutureless procedure. In particular, the aerogel base may be designed to include a device or fixture for attaching the cells or tissue to the aerogel base. Such devices could include an eyelet, a seam, a lock-and-key fitting, or a series of raised protuberances between which cells or tissue, particularly nerves, may be placed, or any other non-uniformity in the surface or interior of the aerogel base in which the cells or tissue may be entrapped or secured so as to retain the cell or tissue and promote cell growth. A hollow (e.g., tubular) substrate could be dimensioned with a reverse taper such that tissue, such as a nerve end, when inserted into the hollow bore, is retained and does not easily slip out from the interior of the substrate.

In particular embodiments, the substrate or neuronal circuit board can be used to regenerate and/or mend wounded or severed nerves, including but not limited to, afferent nerves, efferent nerves, mixed nerves, the optic nerve, the lateral pectoral nerve, the musculocutaneous nerve, the median nerve, the upper subscapular nerve, the lower subscapular nerve, the thoracodorsal nerve, the axillary nerve, the radial nerve, the median pectoral nerve, the medial brachial cutaneous nerve, the medial antebrachial cutaneous nerve, the median nerve, the ulnar nerve or the sciatic nerve.

In other embodiments, the substrate or neuronal circuit board of the invention can be used to generate and mend wounded or severed tendons, muscle tissue, skin tissue, cardiac tissue, stomach lining, or gastrointestinal tissue.

In other particular embodiments, the substrate or neuronal circuit board of the invention can be used at site of nerve branching to direct and fuse nerve growth. Such applications include, but are not limited to use in the sciatic nerve and the facial nerves.

In one embodiment, the invention provides a method of promoting cell growth along a pre-determined path comprising the steps of a. Providing a substrate or a neuronal circuit board apparatus of the invention, wherein the substrate or neuronal circuit board apparatus comprises a porous or an aerogel base having one or more cellular adhesion locations; and b. adhering a cell or cells to be grown at one or more cellular adhesion locations of the substrate or the neuronal circuit board;

such that growth of the cell or cells along a pre-determined path on the substrate is promoted.

In another embodiment, the invention provides a method of promoting cell growth along a pre-determined path comprising the steps of a. Providing a substrate or a neuronal circuit board apparatus of the invention, wherein the substrate or neuronal circuit board apparatus comprises a porous or an aerogel base;

b. adhering one type of cell to be grown at one or more cellular adhesion locations of the substrate or the neuronal circuit board;

c. adhering a compatible cell type at a complementary cellular adhesion location; and d. optionally repeating step c or both steps b and c with the same or different types of cells.

In certain embodiments, the a porous or aerogel base further comprises at least one cellular adhesion inhibiting locations

EXAMPLES

The present invention may be further illustrated by the following non-limiting examples. All reagents were used as received unless otherwise noted. Those skilled in the art will recognize that equivalents of the following supplies and suppliers exist, and as such the suppliers listed below are not to be construed as limiting.

Example 1: Preparation of Aerogels and Toxicity Studies

Materials and Methods

Preparation of Pigment-Doped Aerogels:

Two solutions, the first containing 3.85 mL tetramethoxysilane (TMOS), 3-aminopropylsilane and methanol (4.5 mL) and the second one containing methanol (4.5 mL), water (1.5 mL) and a suspension of the metal oxide pigment (4% weight) were cooled in a mixture of dry-ice acetone. The cold solutions were shaken vigorously and were mixed while cold. The resulting sol was immediately poured into molds and gelled within 60 sec while still cold. The gels were aged for 3 hrs then washed once with methanol (once) and four times with acetonitrile using 4-5 times the volume of the gel for each wash. Subsequently, gels were transferred in an isocyanate bath containing 33 g of Desmodur N3200 (Bayer) in 94 mL of acetonitrile. The volume of the bath was again 4-5 times the volume of each gel. After 24 hrs, the gels were transferred in fresh acetonitrile and they were heated at 70° C. for 72 hrs. At the end of the period, the gels were washed another four times with fresh acetonitrile (24 hrs each time) and they were dried supercritically using liquid $CO_2$. Chromium oxide (green), iron-oxide (red), and cobalt oxide (blue) were the pigments of choice for color-coding the aerogels. All pigments were tested for stability under thermal, vacuum, and UV exposure conditions.

Preparation of Silicone Substrates:

Clear silicone samples were prepared according to the guidelines provided by GE, i.e. a ratio of 10:1 elastomer prepolymer (A) to crosslinker (B) was thoroughly mixed in a Pyrex container, and then completely out gassed in a Precision Scientific No. 6500 vacuum oven for approximately 2 hrs until the mixture had no air bubbles remaining. The mixture was then poured into aluminum molds. They were then transferred to the vacuum oven, outgassed one more time, and finally heat cured at 80° C. for 24 hrs. Once cured and cooled they were removed from the molds and cut into the appropriate dimensions.

OK Cells Preparation

Materials:

Cell culture medium was obtained from MediaTech (Herndon, Va.), fetal bovine serum was from Gibco-InVitrogen (Carlsbad, Calif.) and tissue culture plastic ware was purchased from Corning, Inc. (Corning N.Y.). Basement membrane extract and poly-L-lysine were purchased from R&D Systems (Minneapolis, Minn.).

Methods:

Mammalian Cells:

Opossum kidney cells were maintained in 75 $cm^2$ flasks in Dulbecco's Modified Eagle's Medium/Nutrient Mixture F-12 (DMEM/F12) supplemented with 5% fetal bovine serum (FBS), 100 U/ml penicillin and 100 μg/ml streptomycin. Cells were subcultured weekly using $Ca^{2+}/Mg^{2+}$-free Hank's Balanced salt solution (HBSS) and 0.025% trypsin/0.02% EDTA. Cells were plated at a density of 60,000 cells/ml regardless of the tissue culture vessel. In all cases, aerogels were sterilized by UV (254 nm) on the top of the samples followed by a 5 min wash in 70% ethanol.

Effect of Aerogels on OK Cell Growth:

To assess the effect of aerogels on cell viability, OK cells were grown in the presence and absence of pigmented and non-pigmented (clear) aerogels. To better assess the effect of aerogels on cell behavior experiments were run in parallel with an inert and nonreactive silicone known as RTV 655 (data not shown). Photographs were taken of each aerogel/OK cell co-culture immediately after plating, 24 hrs, and finally 48 hrs later. To assess the ability of OK cells to grow on aerogels, the aerogels were fixed to the bottom of the well of a six well dish using 2% agarose. Opossum kidney cells were then pipetted onto the aerogels and allowed to attach for 24 hrs. Twenty-four and 48 hrs later, aerogels were stained 5 min with crystal violet (0.04% in 4% ethanol), washed 3 times in PBS then photographed for gross determination of patterned cell growth. Although cells did grow in colonies on the surface of the aerogel segments due to difficulty in imaging the surface those pictures are not shown. To assess the impact of co-culture on OK cell growth, aerogels were removed after 48 hrs of co-culture and the monolayer were stained 5 min with crystal violet (0.04% (w/v) in 4% ethanol), washed 3 times in PBS then photographed for gross determination of patterned cell growth.

Effect of Basement Membrane (BME) Extract and Poly-L-Lysine on Directed Growth:

To determine if OK cells could grow in specific patterns on non-tissue culture plastic, basement membrane extract (BME; 12-18 mg/ml) or poly-L-lysine (0.1 mg/ml) was spotted in 20 μl aliquots on polystyrene dishes to promote adhesion in specific regions. Dishes were dried for 2 hrs and cells were then plated and incubated 4 hrs at 37° C. At 4 hrs, cells that had not attached were remove by washing the dishes 3 times with growth medium (DMEM/F12+5% FBS). Photographs were taken at 4 hrs, then 24 and 48 hrs later. At 48 hrs, cells were stained 5 min with crystal violet (0.04% in 4% ethanol), washed 3 times in PBS then photographed for gross determination of patterned cell growth.

*Bacillus* Bacteria Preparation:

Clear aerogel substrates of approximately 1 cm long and 3 mm thick were soaked for 10 min in 70% isopropyl alcohol and then sequentially rinsed four times in fresh sterile deionized water (SDIW) for 10 min in each wash. The substrates were dried for 2 hrs in a laminar flow hood and then sterilized under 254 nm UV irradiation for 1 hr on each side. The UV flux was 2 $\mu m^{-2}$ on the top of the samples. The sterilized aerogel samples were then placed on fresh trypticase soy agar (TSA) plates and incubated for 72 hrs at 30° C. Then, 100 μl of a $2 \times 10^6$ cfu/ml suspensions of the two bacteria were placed on fresh TSA, and spread uniformly around the upper surface of the TSA. The aerogel coupons were immediately transferred to the seeded "lawns" of bacterial cells. Plates were incubated at 30° C. for 96 hrs and visually inspected for any inhibition of bacterial growth. The two species tested were: (a) *Bacillus subtilis* HA1010, and (b) *Serratia liquefaciens* ATCC 27592.

UV-Vis tests: Aerogel segments of ~1 cm×1 cm×2 mm, pigmented and clear were placed in glass beakers each containing 50 ml of deionized water (DI), acetonitrile, IPA, and PBS. Chemicals were purchased from Sigma-Aldrich. Each beaker was covered with parafilm to prevent contamination and loss of solvent through evaporation. Every seven days samples of the solvents containing each type of aerogel were scanned for 1 min by a Beckman-Coulter System Gold 168 photodiode array detector from 200 to 600 nm. Controls of all the solvents were run as well to ensure that leaching due to the beakers themselves did not occur. Two samples were run out of each beaker every week. Each scan was then analyzed using 32 Karat software to determine if there were any peaks for unknown materials. All scans were done at a temperature of 19-23° C.

Figure 2:
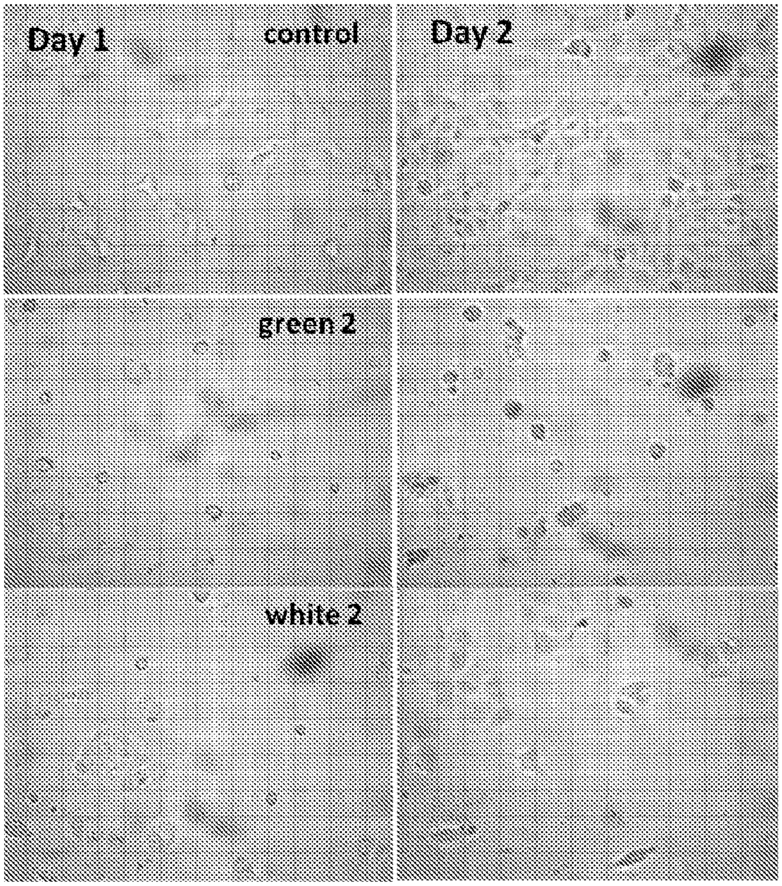
FIG. 2 is a 40× zoomed depiction of the effect of floating aerogels on OK Cell Growth: OK cells were plated in 6 well dishes in the absence (A: control) or presence (B, C) of aerogels clear or with green pigmentation. Photographs (40×) were then taken 24 and 48 hrs later.

Results and Discussion:

Toxicity of Aerogels:

FIG. 1 shows the effects of co-culturing clear and pigmented aerogels with OK cells. The sterilization and culture procedures shift the color of the clear aerogels towards a yellow tint (FIG. 1*a*). After 4 days in culture, the aerogels were removed and the OK cell monolayers were stained with crystal violet (FIG. 1*b, c*). In control wells lacking aerogels (well 1, FIG. 1), there was uniform staining indicating a confluent monolayer of cells. In wells 2-5, (FIG. 1) there was substantially less staining, suggesting either a toxic effect of the aerogels or that the aerogels presented a physical barrier to gas and nutrient exchange. FIG. 2 shows the effect of floating aerogel co-culture on OK cell morphology. One day after plating, cells grown in the absence of an aerogel sample (FIG. 2*a*) had extended processes and formed clusters of cells. After 2 days, cells had substantially increased in number and filled out most of the visual field. Cells grown in the presence of green (CrO) aerogel(s) (FIG. 2*b*) had some cell processes after one day in culture, but did not approach the cell density observed in control cells after two days in culture. Cells grown in the presence of the clear aerogel (FIG. 2*c*) looked most comparable to control cultures; they had extended cell process by day 1 and there were a large number of cells in the visual field.

Figure 3:
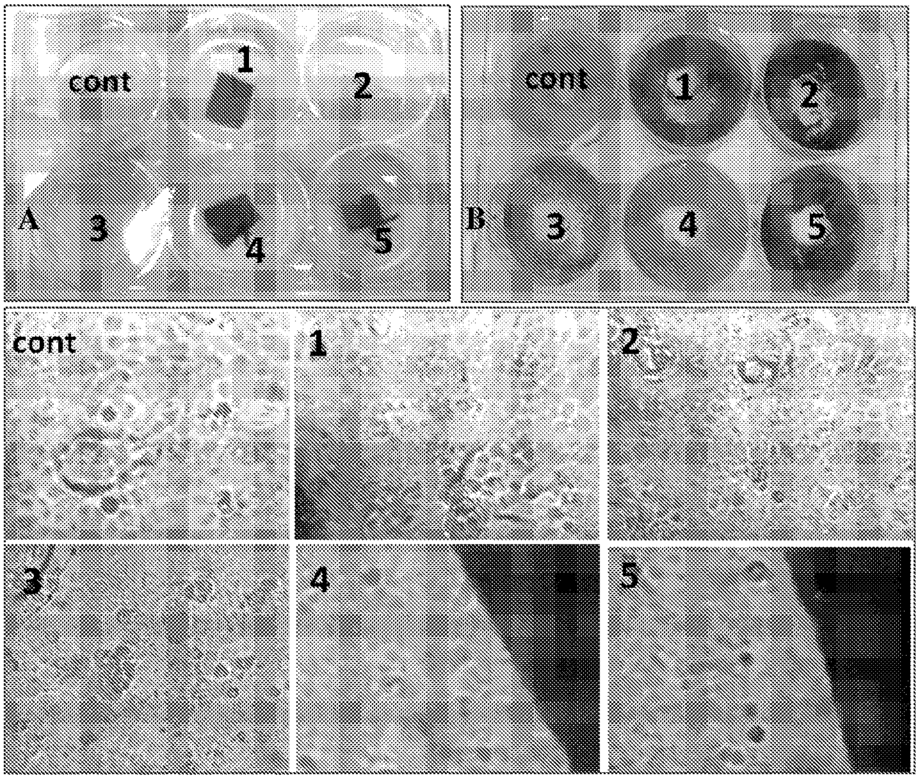
FIG. 3 is a depiction of sample wells showing the effect of attached aerogels on OK cells growth: aerogels were attached to the surface of the tissue culture plastic using 2% agarose. (A) Arrangement of aerogels following fixation to the dish. The numbers of each well correspond to the images in (B) and (C). Control cells had an equal volume of agarose placed in the well. (B) Forty-eight hrs after initiating the cultures, the aerogels were removed and the dishes were stained with 0.04% crystal violet to show cell distribution in the well. (C) prior to removing the aerogels, 40× pictures were taken to assess the growth of OK cells in direct contact with the margins of the aerogels. Opaque regions in 4 and 5 are the edges of the aerogels.

To circumvent the effect of floating aerogels in gas/nutrient exchange blue, green, clear, and red aerogels were fixed to the tissue culture plastic using 2% agarose (FIG. 3*a*). In control cells, a volume of agarose equal to that used to attach the aerogel was placed in the well. After 4 days, aerogels were removed and the OK monolayers were stained with 0.04% crystal violet (FIG. 3*b*). There was uniform staining in controls and all 4 aerogel conditions indicating confluent monolayer of cells in the absence and presence of aerogels. When the cultures were examined microscopically (FIG. 3*c*), no effect of the aerogels on the gross morphology of OK cells was observed.

Figure 4:
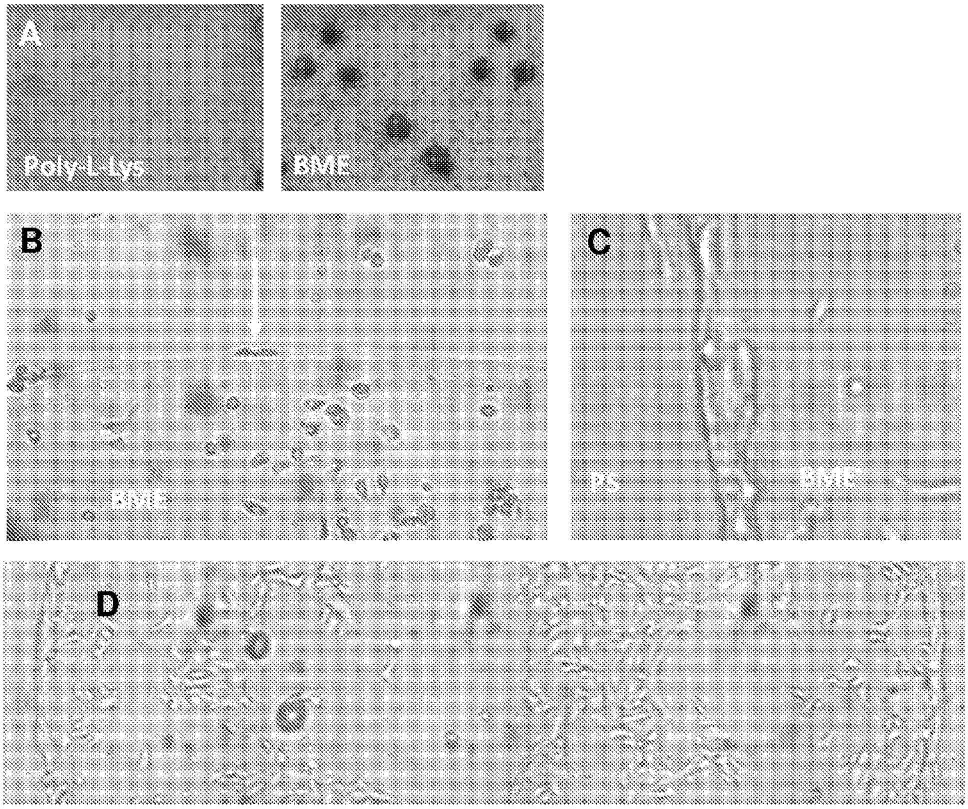
FIG. 4 is a depiction of sample wells showing the effect of basement membrane extract on localized OK Cell growth: poly-L-Lysine and BME was employed (A) 3 days after plating, poly-L-Lys had not produced localized growth of OK cells. In contrast, BME caused OK cell growth in restricted regions. (B) 4 hrs after plating, OK cells aligned at the boundary between the polystyrene dish (PS) and the spot of BME (arrow) (40×). (C) PS-BME interface after 24 hrs (400×). (D) OK cell growth across an entire drop of BME (40×)
Figure 5:
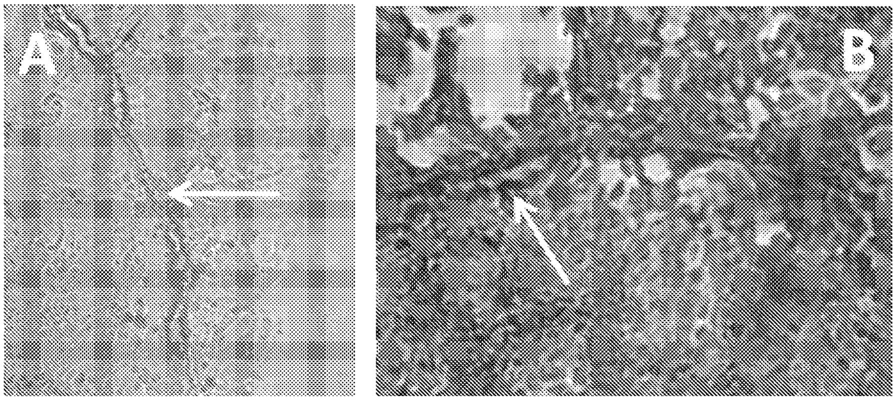
FIG. 5 is a magnification of OK cell growth after escape from long-term directed growth: five days after plating on BME-treated polystyrene plates, OK cells have crossed over the margin produced by the BME droplet and begun growing on the polystyrene. (A) low magnification (40×) of OK growing over the BME-polystyrene border (arrow) (B) higher magnification (400×) shows that there is a two cell-layer border between the BME and the polystyrene.

Effect of Poly-L-Lysine and BME on the Directed Growth of Ok Cells:

A total of 20 μl of poly-L-lysine or BME were spotted in patterns on polystyrene dishes which were not tissue-culture treated. After drying and washing as described in Methods, OK cells were plated. Four hrs later, the dishes were washed and residual cells attached to the spots of poly-L-lysine and BME were photographed. Applying poly-L-lysine in this manner did not promote patterned attachment of OK cells to the polystyrene dishes (FIG. 4*a*). BME did produce localized growth of cells. As early as 4 hrs after plating, cells lined up along the BME-polystyrene interface (FIG. 4*b*). Cells within the area of the BME spot attached and sent out processes while cells on the bare polystyrene did not. After 2 days, several layers of cells had lined up at the BME-polystyrene interface and small colonies of cells were observed within the area of the BME spot (FIG. 4 *c,d*). After 5 days in culture, the polystyrene dishes spotted with poly-L-lysine had OK cells spread over the entire dish (FIG. 4*a*) while the BME cells were concentrated in patterns and in small discrete colonies outside the confines of the BME drops. When examined, the colonies of OK cells by light microscopy, the margins of the BME spot were still visible, but cells had migrated across the BME-polystyrene boundary (FIG. 5). The data presented in FIGS. 4 and 5 show that cell growth can be restrict to defined areas.

Figure 6:
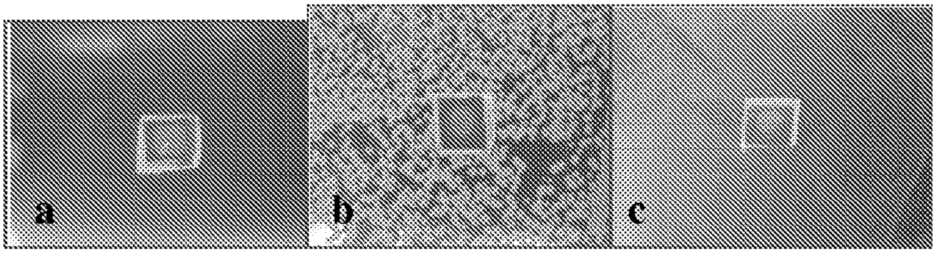
FIG. 6 is a depiction of the effect of clear aerogel on localized *bacillus* growth of strains (c) *Serratia liquefaciens* (ATCC 27592) and (b) *Bacillus subtilis* (HA101): (a) sterilized clear aerogel coupon incubated at 30 C for 4 d. The aerogel was sterilized after exposure to 254 nm of UV radiation. No bacteria have grown from within the aerogel substrate after sterilization step. The opaque white spots in the centers of the aerogel coupons are artifacts caused by placing concave aerogel coupons onto the TSB media; they are not locations of contamination.

Effects of Aerogels on Bacterial Growth:

The sterilization protocol for clear aerogel was found to effectively eliminate microbial contamination on the surface of the material (FIG. 6*a*). No bacterial growth was observed on four of four coupons. The diameters of void spaces in aerogel are generally less than a few 100 nanometers, and thus, bacterial contamination on aerogels must reside on the surface because most prokaryotes are going to persist as cells with minimum dimensions measured ≥400 μm in diameter. In addition, placing pre-sterilized clear aerogel coupons onto seeded lawns of *S. liquefaciens* (FIG. 6*b*) and *B. subtilis* (FIG. 6*c*) failed to generate inhibition zones around the aerogel coupons. Thus, the clear aerogel coupons tested here did not inhibit bacterial growth. Colony morphology and color of both species were unaffected by aerogel over the course of the 4 d of incubating cultures at 30° C.

Effect of Solvents on Pigmented and Non-Pigmented Polyurea Aerogels:

After 7 weeks of aerogel sample immersion in solvent environments (IPA, DI, PBS, acetonitrile) no detectable peaks were observed in the range of 200-600 nm. This leads us to believe that during this period of time a traceable amount of material did not "leach" off the aerogel segments.

Figure 7:
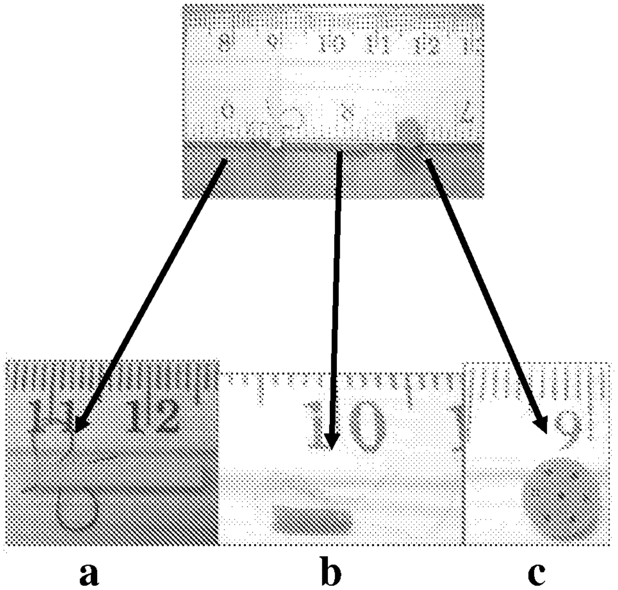
FIG. 7 is a depiction of the structures designed from (a) clear and (b), (c) pigmented aerogels. The scale is in centimeters. None of the structures show any signs of mechanical failure after the machining stage. A gold thread passes through the openings created with ease.

Polyurea coated aerogels can also be manipulated by heavy machinery in order to construct relatively small structures such as those photographed in FIG. 7. No lubricants or cooling jets of water was necessary when cutting these structures.

Example 2: Preparation of Substrates and Neuronal Circuit Boards

Making of Aerogel Substrates:

Two solutions, the first containing 3.85 mL tetramethoxysilane (TMOS), 3-aminopropylsilane and methanol (4.5 mL) and the second one containing methanol (4.5 mL), water (1.5 mL) and a suspension of the metal oxide pigment (4% weight) were cooled in a mixture of dry-ice acetone.

The cold solution was shaken vigorously and was mixed while cold. The resulting solution was immediately poured into molds and gelled within 60 seconds while still cold.

The gels were aged for 3 hours and subsequently washed once with methanol and four times with acetonitrile using 4-5 times the volume of the gel for each wash. Subsequently, gels were transferred in an isocyanate bath containing 33 g of Desmodur N3200 (Bayer) in 94 mL of acetonitrile. The volume of the bath was again 4-5 times the volume of each gel.

After 24 hours, the gels were transferred in fresh acetonitrile and they were heated at 70° C. for 72 hours. At the end of the period, the gels were washed another four times with fresh acetonitrile (24 hours each time) and they were dried using liquid $CO_2$, taken out at the end supercritically (M. Hobbs, R. S. Duran, N. Leventis, L. A. Capadona "Isocyanate-Crosslinked Metal Oxide-Doped Silica Aerogels in Chromatic Calibration Targets for Planetary Exploration," *PMSE Preprints* 2006, 94, 569.)

Making of Circuit Board Pattern on Aerogel Substrate:

The pattern for growth of nerves on the aerogel substrate is formed by means of optical and e-beam lithography or, by means of physical or mechanical etching of grooves and trenches onto the substrate with machine shop tools.

The grooves and channels are then filled or coated with adhesion promoting materials and growth factors. An adhesion inhibiting material may be applied to the surface of the aerogel substrate before or after the application of adhesion promoting materials.

For a finer, more detailed pattern the combination of mechanical machining, optical lithography, and e-beam lithography can be performed in order to fine tune the pattern and moving from one scale and magnitude to a smaller more detailed one.

Figure 12:
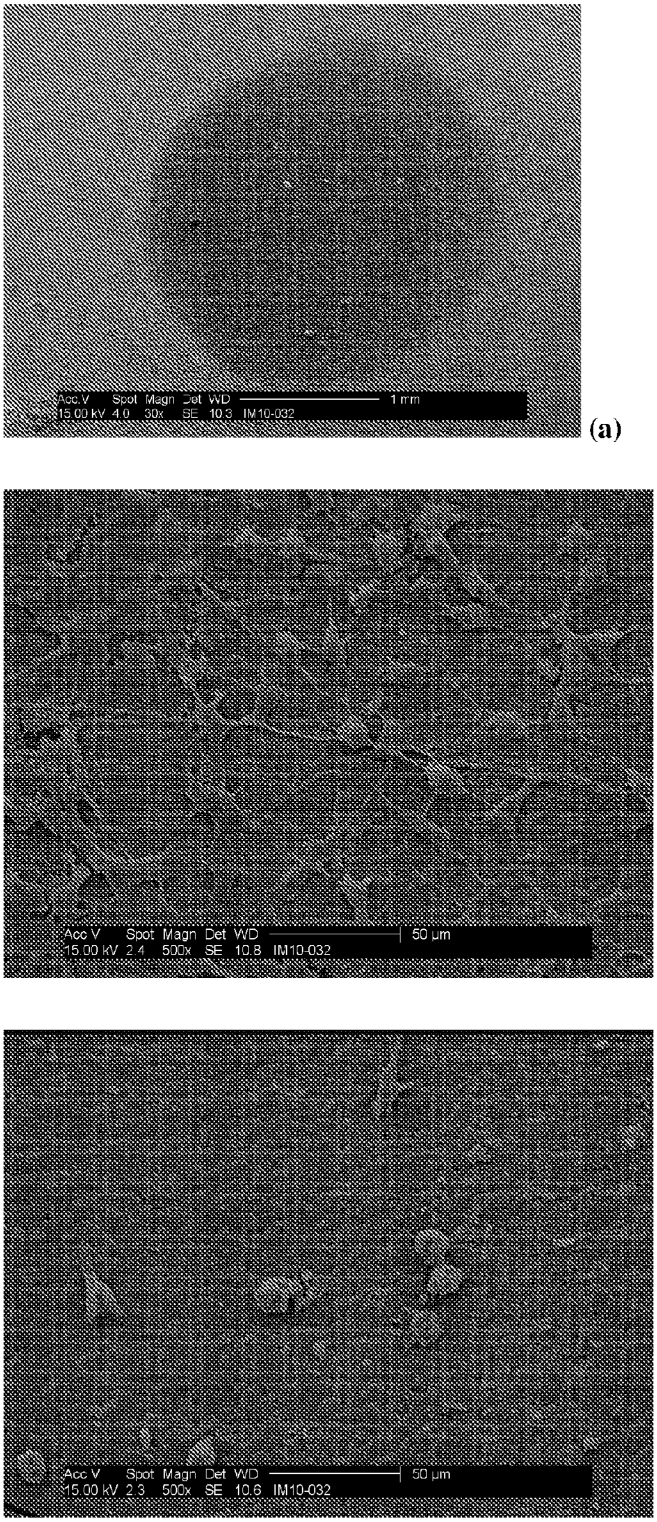
FIG. 12. depicts a SEM micrograph of a laminin coating spot on clear silica aerogel after fixing stage. Dorsal root ganglia cells have been adhered to the laminin coating. a) The boundary of the laminin coating can be clearly seen. b) Dorsal root ganglia cells have grown to a healthy concentration on regions where laminin was deposited and are shown having produced axons which are able to communicate with surrounding cells. c) Sparse to no cell grown can be seen on regions of the aerogel surface that do not have the laminin coating.

In FIG. 12, a silica aerogel substrate as described above was prepared and laminin was added to the surface thereof in a circular pattern. FIG. 12 depicts a SEM micrograph of a laminin coating spot on clear silica aerogel after fixing stage. Dorsal root ganglia cells have been adhered to the laminin coating. a) The boundary of the laminin coating can be clearly seen. b) Dorsal root ganglia cells have grown to a healthy concentration on regions where laminin was deposited and are shown having produced axons which are able to communicate with surrounding cells. c) Sparse to no cell grown can be seen on regions of the aerogel surface that do not have the laminin coating. FIG. 12 demonstrates that nerve growth can be confined to a specific pattern in vitro.

Example 3: Tests for Monitoring Motory Nerve Recovery

Figure 10:
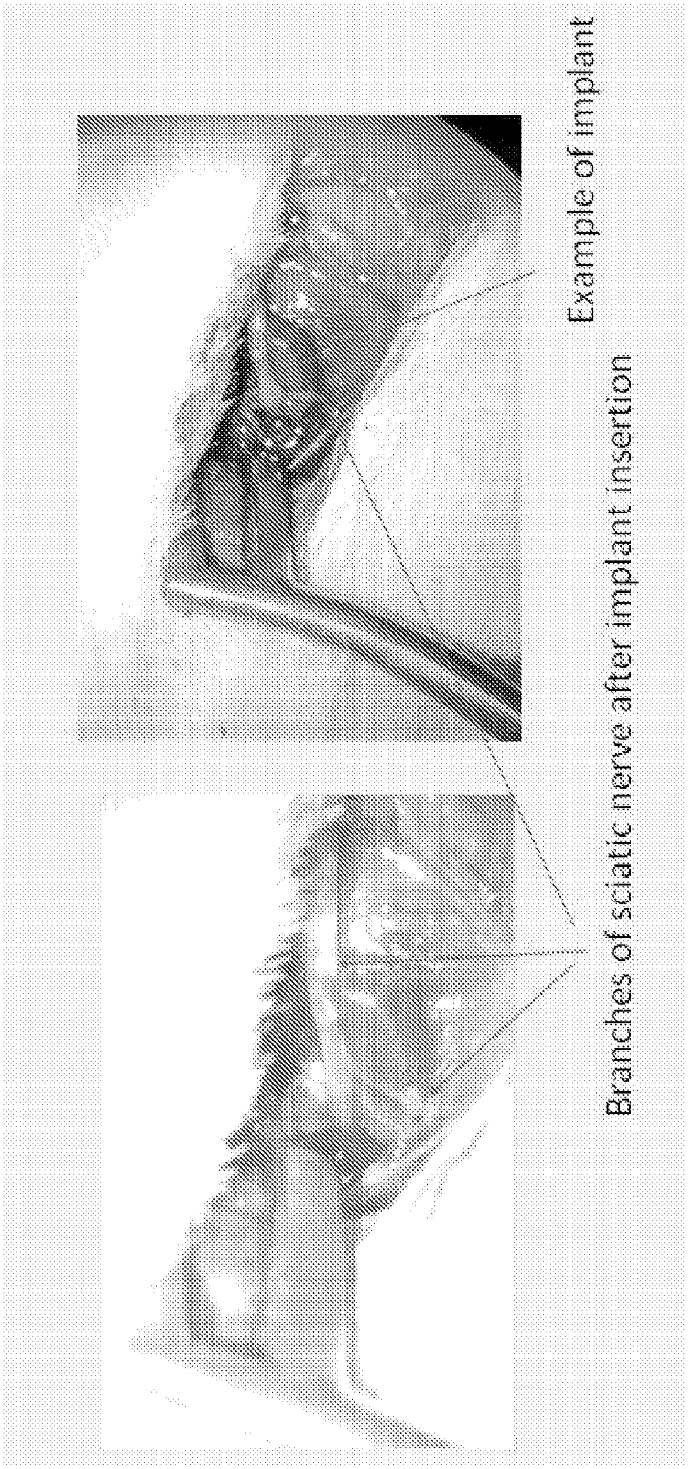
FIG. 10 depicts the implantation of a red-tinted, aerogel base substrate of the invention in the rear hind leg of a female Sprague Dawley rat.
Figure 11:
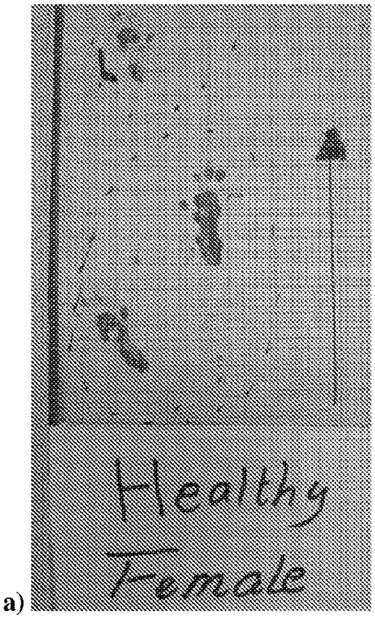
FIG. 11 depicts the hind leg print recorings of a) a healthy female Sprague Dawley rat; b) a female Sprague Dawley rat having a severedsciatic nerve; c) a female Sprague Dawley rat having a severed sciatic nerve repaired by standard suture techniques after several months; and d) a female Sprague Dawley rat having a severed sciatic nerve repaired by an aerogel based substrate of the invention after several months.
Figure 11:
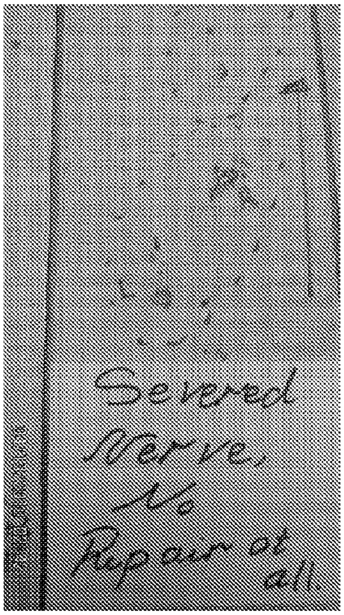
Figure 11:
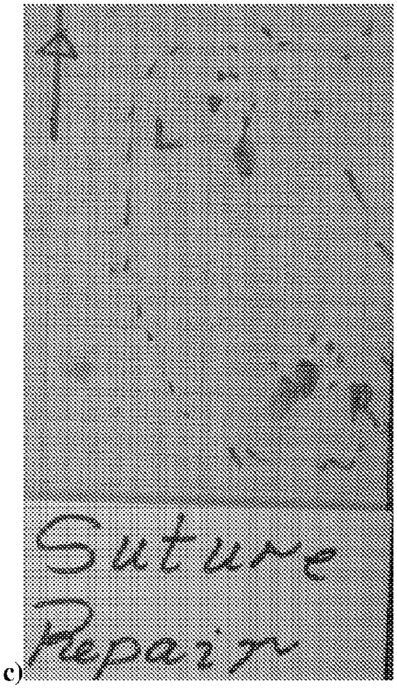
Figure 11:
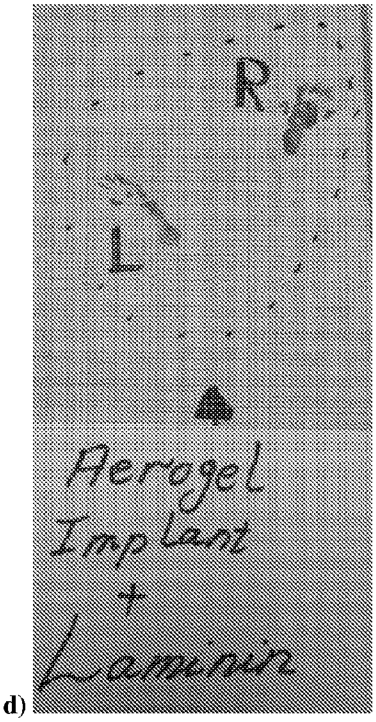

A severance in the left, hind, sciatic nerve of a female Sprague Dawley rat was surgically induced at the branching site. The proximal and distal nerve stumps of the branching site of the sciatic nerve was positioned on the predetermined channels and adhered to an aerogel neuronal circuit board implant as described in Example 2 about 2 mm from the edge of the implant device of the present invention with laminin (FIG. 10).

For control purposes, severance in the sciatic nerve of a female Sprague Dawley rat was surgically induced at the branching site and repaired using a standard suture techniques.

To monitor the recovery of the motor neurons after surgery the hind feet of each female rat was dipped in non toxic paint and then the rat was released on a "rat walk" track, lined with chart paper. The animal would walk away from the stimulus (light) and towards the dark shelter provided at the opposite end. By monitoring the amount of surface area of the foot coming into contact with the graph paper as well as the weight distribution on the hind legs it is possible to track the progress of the recovery after implant insertion. The implant repair foot prints were compared with footprints obtained from healthy rats of the same weight and breed. All foot prints were then compared with those obtained from a rat that underwent nerve severance surgery but did not receive any nerve repair treatments (See, FIG. 10). All surgeries were performed on or around the same date.

The foot prints demonstrate better/more contact with of the sole of the foot with the graph paper showing more control over foot motion. Curled up toes, and partial usage of the paw surface demonstrates existence and extent of injury. As the animal recovers from the nerve severance due to the implant, the foot print obtained would look closer and closer to the ones obtained prior to surgery.

All rats receiving neuronal circuit board implant demonstrated normal behavior with regard to eating, sleeping and drinking post surgery. After several months of implant being inserted in the animals, rats receiving neuronal circuit board implants were observed to have normal behavior and health.

Example 4: Tests for Monitoring Motory Nerve Recovery

A severance in the left, hind, sciatic nerve of a female Sprague Dawley rat is surgically induced at the branching site. The proximal and distal nerve stumps of the branching site of the sciatic nerve are positioned on the predetermined channels and are adhered to an aerogel neuronal circuit board implant as described in Example 2 about 2 mm from the edge of the implant device of the present invention with laminin.

For control purposes, severance in the sciatic nerve of a female Sprague Dawley rat is surgically induced at the branching site and repaired using a standard suture techniques.

The assessments of return of sensory nerve function are performed by standard means as described in De Koenig et al., *Journal of the Neurological Sciences,* 1986, 74:237-246.

According to the published method electrical stimulation is applied to the toe and sole region of the healthy foot of each rat. By contacting the electrodes to the sole of the foot the circuit is closed. The animal's response time is monitored as she withdraws the foot from the probes. This response time is compared with the that measured when the same stimulation is applied to the foot that is recovering from surgery. As the nervous system is repaired the response time is measured.

EQUIVALENTS AND INCORPORATION BY REFERENCE

Those skilled in the art will recognize, or be able to ascertain using no more than routine experimentation, many equivalents to the specific embodiments of the invention described herein. Such equivalents are intended to be encompassed by the following claims.

All references cited herein, whether in print, electronic, computer readable storage media or other form, are expressly incorporated by reference in their entirety and may be employed in the practice of the invention, including but not limited to, abstracts, articles, journals, publications, texts, treatises, technical data sheets, manufacturer's instructions, descriptions, product specifications, product sheets, internet web sites, databases, patents, patent applications, and patent publications.

REFERENCES

1) Bellamkonda R, Aebischer P. Tissue engineering in the nervous system. In: Bronzino J D, editor. Biomedical engineering hand book. Boca Raton, Fla.: CRC Press; 1995. p. 1754-73.

2) Perego G, Cella G D, Aldini N N, Fini M, Giardino R. Preparation of a new nerve guide from a poly(l-lactide-co-6-caprolactone). Biomaterials 1994; 15(3):189-93.

3) Pham H N, Padilla J A, Nguyen K D, Rosen J M. Comparison of nerve repair techniques: suture vs avitene-polyglycolic acid tube. J Reconstr Microsurg 1991; 7:31-6.

4) Kiyotani T, Tevamachi M, Takimoto, Nakamura T, Shimuzu Y, Eudo K. Nerve regeneration across a 25 mm gap bridged by a polyglycolic acid-collagen tube: a histological and electrophysiological evaluation of regenerated nerves. Brain Res 1996; 740: 66-74.

5) Weiss P, Davis H. Pressure block in nerves provided with arterial sleeves. J Neurophysiol 1943; 6:269-86

6) Weiss P. The technology of nerve regeneration: sutureless tubulization and related methods of nerve repair. Neurosurgery.

7) Koyama, H.; Goodpasture, C.; Miller, M. M; Teplitz, R. L.; Riggs, D. Establishment and characterization of a cell line from the American opossum (*Didelphis virginiana*). In Vitro 14:239-246, 1978

8) Hammerman, M. R.; Miller, S. B. Growth factors and regeneration of epithelial cells In: Contemporary Issues in Nephrology: Acute renal failure—new concepts and therapeutic strategies. Churchill Livingstone, Publisher Goligorsky, M. S.; Stein, J. S., editors New York, N.Y., 1995

9) M. J. Burchell, S. A. J. Fairey, N. J. Foster, M. J. Cole Hypervelocity capture of particles in aerogel: Dependence on aerogel properties, Planetary and Space Science 57 (2009) 58-70

10) Paul, H. L., Diller, K. R. Comparison of Thermal Insulation Performance of Fibrous Materials for the Advanced Space Suit *Journal of Biomechanical Engineering, Volume* 125, *Number* 5 (2003) pp 639-647

11) Nicholas Leventis, Three-dimensional core-shell superstructures: Mechanically strong aerogels, *Acc. Chem. Res.,* 40 (9), 874-884.

12) Holt, J. G., Krieg, N. R., Sneath, P. H. A., Staley, J. T., Williams, S. T. 2000. Bergey's Manual of Determinative Bacteriology. Lippincott Williams & Wilkins, Philadelphia, Pa., pp 787.

13) Schuerger, A. C., Mancinelli, R. L., Kern, R. G., Rothschild, L. J., and McKay, C. P. 2003. Survival of endospores of *Bacillus subtilis* on spacecraft surfaces under simulated martian environments: Implications for the forward contamination of Mars. Icarus 165, 253-276.

14) Sonenshein, A. L., Hoch, J. A., and Losick, R. 2002. *Bacillus subtilis* and Its Closest Relatives. ASM Press, Washington, D.C., pp 629.

What is claimed as new and desired to be protected by Letters Patent of the United States is:

1. A substrate for nerve cell growth, comprising:

an aerogel base having a top surface, a first end of the top surface comprising first cellular adhesion locations to which a first plurality of neurons adhere, and a second end of the top surface comprising second cellular adhesion locations to which a second plurality of neurons adhere, wherein the top surface includes one or more nerve cell growth patterns; the first cellular adhesion locations and the second cellular adhesion locations are situated at ends of the one or more nerve cell growth patterns, such that the one or more nerve cell growth patterns direct nerve cell growth from the first end to the second end and/or from the second end to the first end along the one or more nerve cell growth patterns, wherein the one or more nerve cell growth patterns include one or a plurality of nerve cell adhesion promoting locations;

wherein the nerve cell adhesion promoting locations comprise a nerve cell adhesion promoting material selected from the group consisting of: laminin, poly-L-lysine, polyphenolic proteins, MAC-2 binding protein, laminin 10/11, albumin/glutaraldehyde tissue adhesive, fibrin tissue adhesive, cyanoacrylate-based tissue adhesive, proteinaceous adhesive, and basement membrane extract (BME).

2. The substrate for nerve cell growth of claim 1, in which the aerogel base is a hydrophobic aerogel base.

3. The substrate for nerve cell growth of claim 2, in which the hydrophobic aerogel base is a silica aerogel base.

4. The substrate for nerve cell growth of claim 2, in which the hydrophobic aerogel base is crosslinked with a polyurea.

5. The substrate for nerve cell growth of claim 1, in which the base is in the form of an implant.

6. The substrate for nerve cell growth of claim 5, in which the implant is in the form of a cell-scaffold implant, a joint-scaffold, or a stent.

7. The substrate for nerve cell growth of claim 1, wherein the first end and/or second end comprises at least two cellular adhesion locations.

8. The substrate for nerve cell growth of claim 7, wherein the first end and/or the second end comprise at least four cellular adhesion locations.

9. The substrate for nerve cell growth of claim 1, wherein two or more cellular adhesion locations are complementary for the same cell type.

10. The substrate for nerve cell growth of claim 1, wherein at least two sets of complementary cellular adhesion locations are complementary for different cell types.

11. The substrate of claim 1, in which complementary cellular adhesion locations are color coded to identify the start and end of a directional growth pattern.

12. The substrate or neuronal circuit board apparatus of claim 11, in which the pre-printed directional growth pattern is color coded to identify the directional growth pattern associated with complementary cellular adhesion locations.

13. The substrate for nerve cell growth of claim 1, wherein the first plurality of neurons includes a first end of one or more neurons and the second plurality of neurons includes a second end of the one or more second neurons.

14. The substrate for nerve cell growth of claim 13, wherein the one or more neurons are selected from the group consisting of an afferent nerve, an efferent nerve, an optic nerve, a lateral pectoral nerve, a musculocutaneous nerve, a median nerve, an upper subscapular nerve, a lower subscapular nerve, a thoracodorsal nerve, an axillary nerve, a radial nerve, a median pectoral nerve, a medial brachial cutaneous nerve, a medial antebrachial cutaneous nerve, a median nerve, an ulnar nerve and a sciatic nerve.

15. The substrate for nerve cell growth of claim 13, wherein the one or more neurons are a sciatic nerve.

16. The substrate for nerve cell growth of claim 1, wherein the substrate is a geometric shape selected from the group consisting of a square, rectangle, and oblong, a diamond, a triangle, a circle, and an oval.

17. The substrate for nerve cell growth of claim 1, wherein the substrate has a thickness ranging from 1 μm to 100 μm.

18. The substrate for nerve cell growth of claim 17, wherein the substrate has a thickness ranging from 1 μm to 5 μm.

19. The substrate for nerve cell growth of claim 1, wherein the aerogel base is biocompatible.

20. The substrate for nerve cell growth of claim 1, wherein the aerogel base is biodegradable.

21. The substrate for nerve cell growth of claim 1, wherein the aerogel base is tinted.

22. The substrate for nerve cell growth of claim 21, wherein the tinting is due to a pigment selected from the group consisting of chromium oxide, iron-oxide, and cobalt oxide.

23. The substrate for nerve cell growth of claim 1, wherein the aerogel base includes an attachment fixture selected from the group consisting of an eyelet, a seam, a lock-and-key fitting, and one or more raised protuberances.

24. The substrate for nerve cell growth of claim 1, wherein the aerogel base includes one or more hollow channels or tubes configured to receive the first plurality of neurons and the second plurality of neurons.

25. The substrate for nerve cell growth of claim 24, wherein a first end of the one or more hollow channels or tubes includes a reverse taper configured to hold and retain a first end of one or more neurons in the first plurality of neurons.

26. The substrate for nerve cell growth of claim 25, wherein a second end of the one or more hollow channels or tubes includes a reverse taper configured to hold and retain a second end of one or more neurons in the second plurality of neurons.

27. The substrate for nerve cell growth of claim 25, wherein a first end of the one or more hollow channels or tubes includes a reverse taper configured to hold and retain a first end of one or more neurons in the first plurality of neurons and a second end of the one or more hollow channels or tubes includes a reverse taper configured to hold and retain a second end of one or more neurons in the second plurality of neurons.

28. A substrate for nerve cell growth, comprising:

an aerogel base having a top surface, a first end of the top surface retaining a first end of one or more neurons, and a second end of the top surface retaining a second end of the one or more neurons, wherein the top surface of the aerogel base includes one or more hollow channels or tubes holding the one or more neurons and connect the first end to the second end, wherein each end of the one or more hollow channels or tubes includes a reverse taper retaining the first end of the one or more neurons or second end of the one or more neurons, wherein the first of the one or more neurons or second end of the one or more neurons are situated at ends of the one or more nerve cell growth patterns, wherein the one or more nerve cell growth patterns direct nerve cell growth from the first end to the second end and/or from the second end to the first end along the one or more nerve cell growth patterns, wherein the one or more nerve cell growth patterns include one or a plurality of nerve cell adhesion promoting locations;

wherein the nerve cell adhesion promoting locations comprise a nerve cell adhesion promoting material selected from the group consisting of: laminin, poly-L-lysine, polyphenolic proteins, MAC-2 binding protein, laminin 10/11, albumin/glutaraldehyde tissue adhesive, fibrin tissue adhesive, cyanoacrylate-based tissue adhesive, proteinaceous adhesive, and basement membrane extract (BME).

* * * * *